United States Patent
Gramatikov et al.

(10) Patent No.: US 10,314,483 B2
(45) Date of Patent: Jun. 11, 2019

(54) FAST X-Y AXIS BRIGHT PUPIL TRACKER

(71) Applicant: THE JOHNS HOPKINS UNIVERSITY, Baltimore, MD (US)

(72) Inventors: Boris I. Gramatikov, Baltimore, MD (US); David L. Guyton, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 107 days.

(21) Appl. No.: 15/446,164

(22) Filed: Mar. 1, 2017

(65) Prior Publication Data

US 2018/0249906 A1    Sep. 6, 2018

(51) Int. Cl.
| | |
|---|---|
| A61B 3/113 | (2006.01) |
| A61B 3/14 | (2006.01) |
| A61B 3/00 | (2006.01) |
| H01J 43/04 | (2006.01) |
| H01J 43/28 | (2006.01) |

(52) U.S. Cl.
CPC ............ A61B 3/113 (2013.01); A61B 3/0025 (2013.01); A61B 3/14 (2013.01); H01J 43/04 (2013.01); H01J 43/28 (2013.01)

(58) Field of Classification Search
CPC ......... A61B 3/113; A61B 3/0025; A61B 3/14; G06K 9/00604; G06F 3/013
USPC ................................................ 351/200–246
See application file for complete search history.

(56) References Cited

U.S. PATENT DOCUMENTS

| | | |
|---|---|---|
| 6,959,102 B2 | 10/2005 | Peck |
| 7,391,887 B2 | 6/2008 | Durnell |
| 8,591,030 B2 | 11/2013 | Grecu et al. |

(Continued)

FOREIGN PATENT DOCUMENTS

WO    2004066097 A2    8/2004

OTHER PUBLICATIONS

Almeida et al., Computer-Aided Methodology for Syndromic Strabismus Diagnosis., (2015) Journal of Digital Imaging, 28(4), 462-473.

(Continued)

*Primary Examiner* — Mohammed A Hasan
(74) *Attorney, Agent, or Firm* — Johns Hopkins Technology Ventures

(57) ABSTRACT

The present invention provides for very fast detection of gaze direction using retro-reflected light from the ocular fundus that is cost-efficient, small, and portable. These eye trackers are useful in many areas of science and technology, including but not limited to remote control, space, defense, medical and psycho-physiological applications, to identify for example subtle neurologic deficits that occur with cerebellar or vestibular disorders, Parkinson's disease, strokes, traumatic brain injury, possible concussions during sports matches, some forms of reading disability, or simply fatigue or inebriation. In ophthalmology, with two such devices operating simultaneously, the variability of relative eye alignment over time can be measured, without requiring individual calibration, and without requiring fixation on a specified target, ideal for use with small children. Such instruments have widespread application as noninvasive screening devices in infants and young children or patients of any age for defects of binocular function such as strabismus and amblyopia.

22 Claims, 15 Drawing Sheets

(56) References Cited

U.S. PATENT DOCUMENTS

| | | | | |
|---|---|---|---|---|
| 2013/0044291 A1* | 2/2013 | Kato | .................... | A61B 3/0025 |
| | | | | 351/209 |
| 2014/0268055 A1* | 9/2014 | Skogo | .................... | A61B 3/113 |
| | | | | 351/210 |
| 2015/0208916 A1* | 7/2015 | Hayashi | ............... | A61B 3/0083 |
| | | | | 351/208 |

OTHER PUBLICATIONS

Long et al., A High Speed Eye Tracking System with Robust Pupil Center Estimation Algorithm., (2007) IEEE EMBC.

* cited by examiner

FAST X-Y AXIS BRIGHT PUPIL TRACKER

FIELD OF INVENTION

The field of the currently claimed embodiments of this invention relates to medical devices, and more particularly to an improved monocular eye position sensor.

BACKGROUND

With advances in user interface technologies and computer-based medical diagnostic methods, there is an increasing demand for accurate, fast, portable and inexpensive eye trackers and fixation monitors. Because eye gaze is a strong indication for current attention and intention, such devices may automatically and accurately estimate: where the person is looking, the current and past areas of attention, the possible intentions and/or the possible neurological stability of a person. Eye tracking thus provides a key input to enable a range of applications and devices that would benefit from utilizing such information. The scope of potential applications is extensive, ranging from medical diagnostics to intuitive and fast man-machine interfacing. Examples include mobile devices, computer interaction in professional environments, security applications, vehicle security and vehicle interaction, air traffic control, computer gaming, etc. Presently, eye tracking already provides great value in commercial and research-related applications such as psychology and vision research, assistive technology, eye-based communication for people with highly limited mobility, commercial usability, and advertising studies, etc.

Gaze direction can be estimated by a variety of techniques, each of them having its advantages and limitations. Most contemporary eye trackers detect eye position, usually employing the reflection of a point light source from the front surface of the cornea (corneal light reflex) relative to the bright or dark pupil (when the eye rotates, the pupil moves about twice as fast as the corneal light reflex, with the differential being a function of the direction and amount of eye movement), or relative to the reflection of the same point light source from the back of the crystalline lens of the eye (fourth Purkinje image).

More precise are the foveal eye trackers. When an individual looks at a target, that target is imaged on the fovea. It is thus foveal fixation that correlates precisely with gaze direction. It has also been shown that landmarks such as the fovea and the optic disc can be detected robustly by measuring the amount of polarization change caused by the surrounding birefringent nerve fibers during double passage of a beam of light through them upon fundus reflection in double-pass systems. Recent research has shown that techniques that effectively track or monitor the optical projection of fundus landmarks out from the eye afford a more direct measurement of fixation direction, and are physiologically more relevant. The major advantage of this new eye-fixation detection and tracking method is that it uses true information coming directly from retinal landmarks, as opposed to existing eye-tracking systems that use reflections from other structures, to identify the direction of foveal gaze.

Current non-invasive video eye trackers use digital, image-based sensors and can be relatively fast and accurate. Among them are the EyeLink 1000 Plus of SR Research (2 kHz max, after a costly upgrade from 1000 Hz), EYE-TRAC 7 of Applied Scientific Laboratories (360 Hz max), TX300 of Tobii (300 Hz max), 3D ETD of Chronos Vision GmbH (400 Hz), Hi-Speed 500 from SensoMotoric Instruments (500 Hz), and others. Yet, they are laboratory instruments that cost tens of thousands of dollars and are either cumbersome tabletop units or delicate, head-mounted devices, unsuitable for use in many patients, especially in children. For many applications in ophthalmology, neurology, otology, and neuro-otology, measurement speeds of several thousand measurements per second are highly desirable, often for an extended period of time, i.e. a minute or more. Example are studying saccades, post-saccadic oscillations, fixation stability with age-related macular degeneration, pursuit eye movement, etc. Acquiring complete digital images at a high frame rate inevitably puts a restriction on the recording time and the throughput of the system. Today, such speed without high bandwidth streaming video can only be provided by the more invasive scleral search coil recordings, which require the subject to sit within a metal antenna frame while a coil of wire is placed on the eye for measurement under exacting conditions. Scleral search coils induce discomfort and impact the eye movement and the ability to maintain convergence. Children cannot tolerate scleral search coils.

All existing eye-tracking instruments are designed to determine and track the direction of gaze of one or both eyes, requiring cooperation by the subject for precise calibration. They usually record the accuracy of fixation on a directed target.

A method and device are therefore needed for fast and accurate eye tracking and fixation monitoring, without requiring digital streaming, storage and manipulation of complete images at high frame rates, but rather acquisition and transmission of only sufficient data needed for X-Y tracking of the pupil.

SUMMARY

The foregoing needs are met, to a great extent, by the present invention wherein in one aspect, a fast device for detecting rapid movements of an eye of a subject by tracking an image of the pupil of the eye includes a light source configured for delivering light to an eye of the subject, wherein the light entering the pupil of the eye is retro-reflected by the fundus of the eye back toward the light source. The device includes optical means for capturing the light retro-reflected by the fundus of the eye to form a bright image of the pupil of the eye. The device also includes a position-sensing detector configured to receive the bright image of the pupil of the eye and to extract only a minimum amount of information necessary to determine the position of the centroid of intensity of said bright image on the detector along only two orthogonal axes. The device includes a means for digital analysis of the minimum amount of position sensing information from the position-sensing detector to generate an output characterizing movements of the eye. The method also includes a means for low-throughput transmission and storage of the minimum amount of information to a digital processing unit.

In accordance with an aspect of the present invention, the position-sensing detector takes the form of an analog duo-lateral position sensor, which may stand alone or may be enhanced by inclusion of an image intensifier for use with low light levels. The image intensifier receives the image of the bright pupil from said optical means and delivers an intensified version of the image of the bright pupil to said duo-lateral position sensor. The image intensifier may be a photodiode array combined with a conjugate array of LEDs, wherein the output of each photodetector is amplified and used to drive the corresponding LED in the conjugate array of LEDs, creating a pixelated rendition of the intensified image for conveyance to the duo-lateral position sensor. Alternatively, the image intensifier may be a coherent microchannel plate serving as an electron multiplier and accelerator for each microchannel in the plate, producing a pixelated rendition of the intensified image for conveyance to the duo-lateral position sensor.

In accordance with another aspect of the present invention, the position-sensing detector includes an array of n×m photodetectors wherein the output signals are not read out individually, but are rather summed in analog manner row-wise and column-wise to build the X- and Y-profiles of the image of the bright pupil, as projections onto the X- and Y-axes, and are digitized as n+m intensity values. The position of the pupil is then determined from the maxima of the X- and Y-profiles in 1D context (one dimension) for the corresponding directions of eye movement to be detected. The maxima of the X- and Y-profiles are determined by 1D interpolation.

In accordance with still another aspect of the present invention, the position-sensing detector includes an array of n×m avalanche photodetectors wherein the output signals are not read out individually, but are rather summed in analog manner row-wise and column-wise to build the X- and Y-profiles of the image of the bright pupil, as projections onto the X- and Y-axes, and are digitized as n+m intensity values. The position of the pupil is then determined from the maxima of the X- and Y-profiles in 1D context (one dimension) for the corresponding directions of eye movement to be detected. The maxima of the X- and Y-profiles are determined by 1D interpolation.

In accordance with still another aspect of the present invention, the position-sensing detector includes a digital n×m profile sensor of n rows and m columns of pixels wherein the output signals are the digitized sums of the n rows and m columns, to build the X- and Y-profiles of the image of the bright pupil, as projections onto the X- and Y-axes. The position of the pupil is then determined from the maxima of the X- and Y-profiles in 1D context (one dimension) for the corresponding directions of eye movement to be detected. The maxima of the X- and Y-profiles are determined by 1D interpolation. For use with low light levels, an image intensifier may be added, for example in the form of a microchannel plate that receives the image of the bright pupil from said optical means and delivers an intensified version of the image of the bright pupil to said profile sensor.

In accordance with still another aspect of the present invention, the position-sensing detector can include two separate linear photodetector arrays aligned respectively along the two orthogonal axes whereby each linear photodetector array receives an image of the bright pupil for detection of the position of the center of said image on the linear photodetector.

In accordance with yet another aspect of the present invention, a method for detecting rapid movements of an eye of a subject by tracking an image of the pupil of the eye, includes delivering light to an eye of the subject. The light entering the pupil of the eye is retro-reflected by the fundus of the eye back toward the light source. The method includes capturing the light retro-reflected by the fundus of the eye to form a bright image of the pupil of the eye. The method includes receiving the bright image of the pupil of the eye and extracting only a minimum amount of information necessary to determine the position of the intensity centroid of said bright image on a detector along only two orthogonal axes. The method includes low-throughput transmitting and storing of said minimum amount of information to a digital processing unit and receiving information from the position-sensing detector to generate an output characterizing movements of the eye.

In accordance with another aspect of the present invention, the method includes receiving the image of the bright pupil from said optical means and delivering the image of the bright pupil to said duo-lateral position sensor. The method includes receiving the image of the bright pupil with an image intensifier from said optical means and delivering an intensified version of the image of the bright pupil to said duo-lateral position sensor. Additionally, the method includes determining maxima on X- and Y-profiles using 1D interpolation. The method includes using an image intensifier with a photodiode array and a conjugate array of light emitting diodes (LEDs). The output of each photodetector is amplified and used to drive the corresponding LED in the conjugate array of LEDs, creating a pixelated rendition of the intensified pupil image for conveyance to the position-sensing detector. The method includes using an image intensifier in the form of a microchannel plate that receives the image of the bright pupil from said optical means and delivers an intensified version of the image of the bright pupil to said profile sensor. The method also includes using a position-sensing detector comprises two separate linear photodetector arrays aligned respectively along the two orthogonal axes whereby each linear photodetector array receives an image of the bright pupil for detection of the position of the intensity centroid of said image on the linear photodetector.

BRIEF DESCRIPTION OF THE DRAWINGS

Further objectives and advantages will become apparent from a consideration of the description, drawings, and examples.

DETAILED DESCRIPTION

The presently disclosed subject matter will now be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention provides a novel class of technologies for very fast detection of direction of gaze using retro-reflected light from the ocular fundus. These technologies provide very fast monocular eye trackers. Some embodiments may be very cost-efficient, small, and portable. With two such devices operating simultaneously, the variability of relative eye alignment over time can be measured (a measure of gaze conjugacy), without requiring individual calibration, and without requiring fixation on a specified target, ideal for use with small children. Such instruments will have widespread application as noninvasive screening devices in infants and young children for defects of binocular function such as strabismus and amblyopia. The technology can also be used with patients of any age.

Figure 1:
FIG. 1 illustrates an 8-bit image of the face when illuminated in the described manner with an 880 nm NIR light emitting diode (NIRLED).
Figure 2:
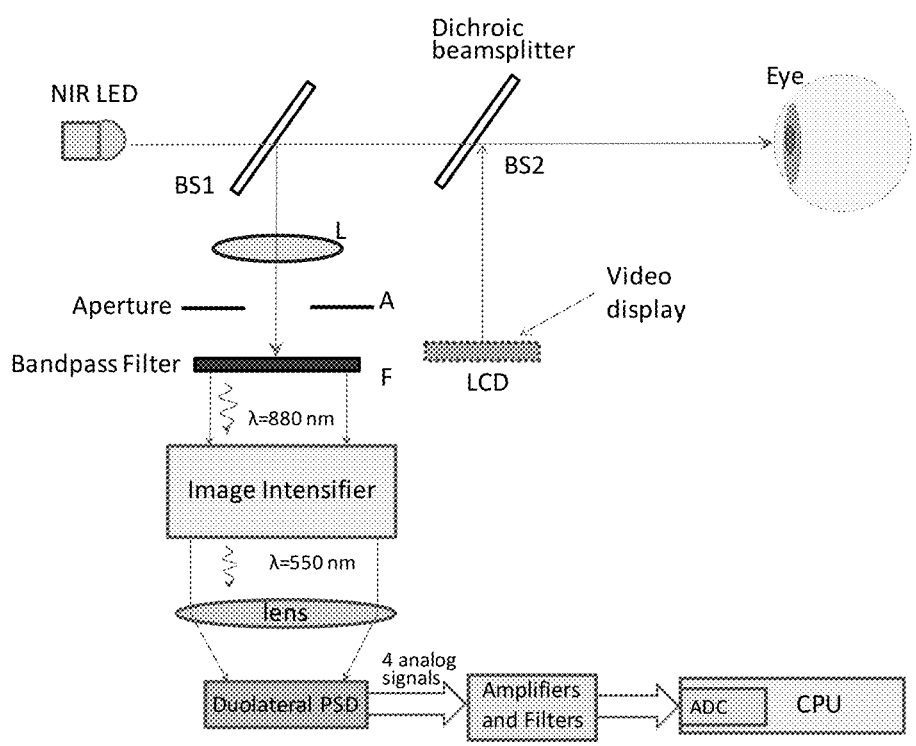
FIG. 2 illustrates a schematic diagram of an eye tracker using an image intensifier containing a photocathode, Microchannel Plate (MCP), an electron accelerator, a phosphor screen and a Fiber Optic Plate (FOP), and an analog duolateral X-Y position sensor.

The present invention includes multiple embodiments for ultra-fast eye-tracking, eye-conjugacy/disconjugacy, and eye-fixation detection, to be used in medical research and diagnostics. When the face is illuminated with a small source of NIR light coaxial with the detection system, the pupils appear bright, because the light reflected from the fundus is imaged by the eyes back toward the small light source and into the detection system, as opposed to the light reflected by the lids, sclera, and iris (and the light highly diverged by the cornea), most of which misses the detection system. The brightest pupils occur when the eyes are focused on a visible target in a plane optically conjugate to the small light source and the returning light beams from the fundi are imaged by the eyes through a small aperture conjugate with the small light source. FIG. 1 illustrates an 8 bit image of the face when illuminated in this way with an 880 nm NIR light emitting diode (NIRLED). The two pupils appear as two bright circles. The instruments to be developed will obtain bright pupils with a small coaxial near infrared light source (for example with wavelength in the range of 780-920 nm) and will image the bright pupil through an aperture conjugate to the light source onto a position sensor, as illustrated in FIG. 2. The subject can watch an attention-attracting movie on the small, computer-controlled LCD video display—with the video display being in a plane optically conjugate to the NIR light source, taking into account the chromatic aberration of the eye (the eye is about 0.75 D more hyperopic for 800 nm light than for visible light). The simultaneous X-Y positions of the bright pupil image are acquired by a position sensor. The sensor may be an analog duolateral X-Y position sensing detector (PSDs) that give the X-Y coordinates of a bright spot (such as a pupil) at any given time, a true image sensor array, or a profile sensor.

Figure 3:
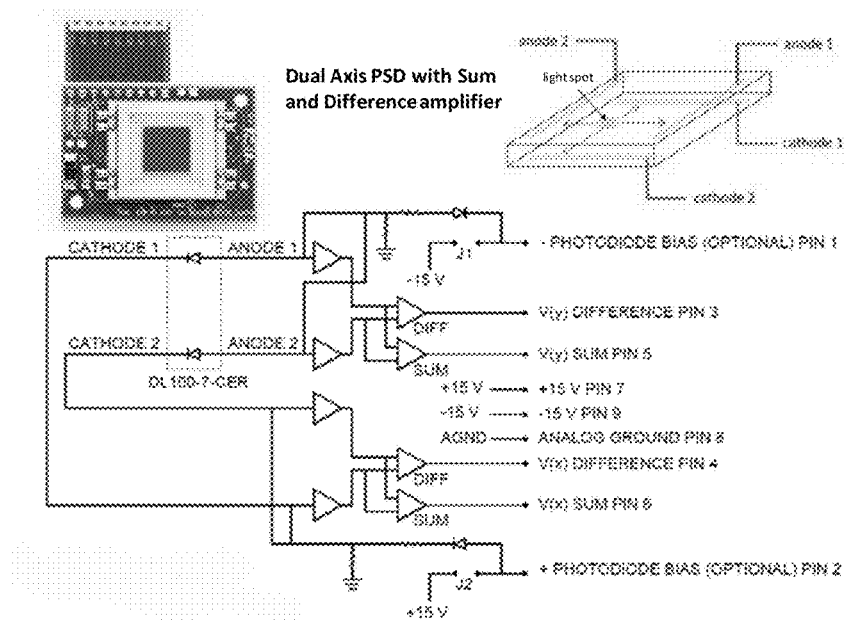
FIG. 3 illustrates a schematic diagram of a dual axis position-sensing detector (PSD) and electrical connections.
Figure 4:
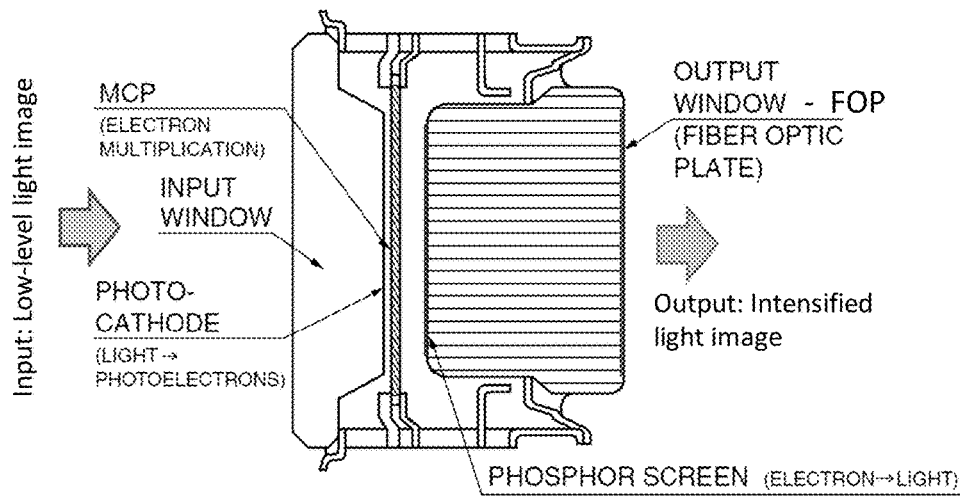
FIG. 4 illustrates a schematic diagram of an exemplary image intensifier.
Figure 5:
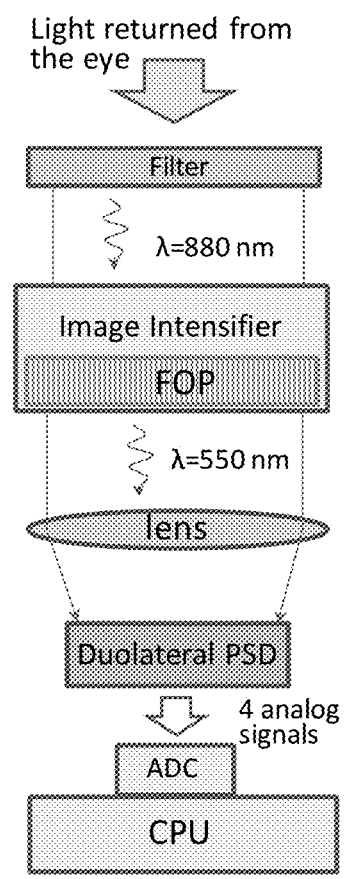
FIG. 5 illustrates a schematic diagram of a receiving portion of an eye tracker. Light reflected from the eye passes through an NIR interference filter (880 nm) and reaches the image intensifier, whose photocathode is IR sensitive.

As illustrated in FIG. 2, an analog duolateral position-sensing detector (PSD) is used. The "entrance pupil" for the eye is imaged onto a 10×10 mm dual-axis (duolateral), highly linear, position-sensing photodetector (FIG. 3). For better contrast at low light levels, the light in the image of the bright pupil may first be intensified by an image intensifier (FIG. 4, FIG. 5). The image intensifier, as explained in more detail below, may convey the intensified image to the PSD directly or to an optical system (lens) to be re-imaged onto the PSD. As light impinges on the PSD, bipolar analog signals are produced, representing the X and Y positions of the centroid of the light power density. The pre-amplifiers and current-to-voltage converters are placed on the sensor boards, near the PSDs. The analog signals of the duolateral PSD (FIG. 2) are then fed to an analog module for analog filtering and final amplification, and from there to an analog-to-digital converter and to a CPU, which can be provided by a PC, a microcontroller, a digital signal processor, or similar device. The eye-tracking process is thus reduced to digitizing two analog signals and two normalizing signals.

The device and method of FIG. 2 can thus operate at very high speed because no sensor array is involved, and the pupil detection process takes place in analog circuitry, all the way to a 4-channel ADC, which can operate at a very high speed, at least an order faster than any video system available today.

Light coming back from the eye is not always sufficient to activate the analog PSD. Because of that, the image intensifier in FIG. 2, and as illustrated more completely in FIG. 4, may be placed between the lens and the analog PSD in FIG. 2, typically an image intensifier of the Generation 2 or 3 non-inverting type. FIG. 4 illustrates a schematic diagram of an exemplary image intensifier. In FIG. 4, the photocathode absorbs the energy of the input light and converts it to electrons. These electrons are then accelerated by a voltage applied between the photocathode and a microchannel plate (MCP). The MCP consists of an array of millions of very thin glass pipes (channels) and serves as a secondary electron multiplier because the input electrons impinging on the channel wall produce secondary electrons, with this process being repeated several tens of times. The electrons multiplied by the MCP are further accelerated by the voltage between the MCP output and a phosphor screen, and then strike the phosphor screen to produce an image that is intensified thousands of times. To achieve speed, the phosphor screen is optimally chosen to have a short decay time (i.e. a decay time of 10-50 μs).

Finally, the image is transferred from the phosphor screen to the output via a fiber optic plate (FOP) serving as an output window. The FOP is comprised of millions of glass fibers of 6 μm diameter, bundled parallel to one another. The FOP is capable of transmitting an optical image from one surface to another without causing any image distortion. One exemplary image intensifier has input/output windows of 13.5×10 mm, with a high IR sensitivity GaAs photocathode, a one stage MCP, and a P24 phosphor screen of decay time of 3 μs to 40 μs). In some embodiments, the image intensifier includes a built-in power supply. Many other image intensifiers do not. In the latter case, the image intensifiers must be provided with a high-voltage power supply, designed as a controllable DC-DC converter. Such power supplies typically include: a power scaling section that receives an input voltage signal and converts the input voltage signal to a controllable DC voltage; a push-pull converter for converting the controllable DC voltage to a high-frequency wave; and a voltage multiplier receiving the high-frequency wave generated by the push-pull converter and performing successive voltage doubling operations to generate a high-voltage DC output. Other image intensifiers known to, or conceivable by, one of ordinary skill in the art may also be used. Image intensifiers are relatively costly devices (ca. $2,000-$6,000). Yet, in combination with the PSD, they allow eye tracking speeds unthinkable with any video systems.

The electrical connection of the duolateral position-sensing detector is shown on FIG. 3. FIG. 3 illustrates a schematic diagram of a dual axis position-sensing detector (PSD) and electrical connections. The figure illustrates a schematic diagram of a dual axis position-sensing detector (PSD) and electrical connections. The detector consists of two photodiodes each with electrodes placed at opposite edges. Two resistive sheets cover the p-n junction, with one sheet on top and one sheet on the bottom. As a spot of bright light impinges on the photodiode, the p-n junction generates a current at the centroid of the light power density. The current from this generator separates at the top resistive sheet according to Ohm's law, and the two electrodes at the opposite ends collect the individual currents. The response at the bottom sheet layer is similar to the top sheet except that the currents are in the orthogonal directions to those in the top sheet because the bottom edge electrodes are placed orthogonal to the top edge electrodes.

Amplifiers are used that convert the light-generated currents into voltages. The voltages are then processed to provide a bipolar signal for the X-axis and a bipolar signal for the Y-axis. The currents are further processed to provide a voltage for the total X current and the total Y current. The sums of currents for X and Y are provided for normalization purposes, as mentioned above.

FIG. 5 illustrates a schematic diagram of the receiving portion of the eye tracker (not to scale). Light reflected from the eye is imaged through an NIR interference filter (880 nm) into an image of the pupil on the image intensifier, whose photocathode is IR sensitive. The phosphor screen of the intensifier emits green light of 550 nm, which is coupled to the PSD by means of a coupling lens. The FOP can also be placed directly onto the position sensor in some embodiments. Although the PSD has only ca. 30% quantum efficiency at 550 nm, the light will be intensified to a level high enough to activate the PSD. In other implementations, a 2-stage MCP is used, representing a third generation image intensifier which is capable of providing ca. 10 times more gain.

Figure 6:
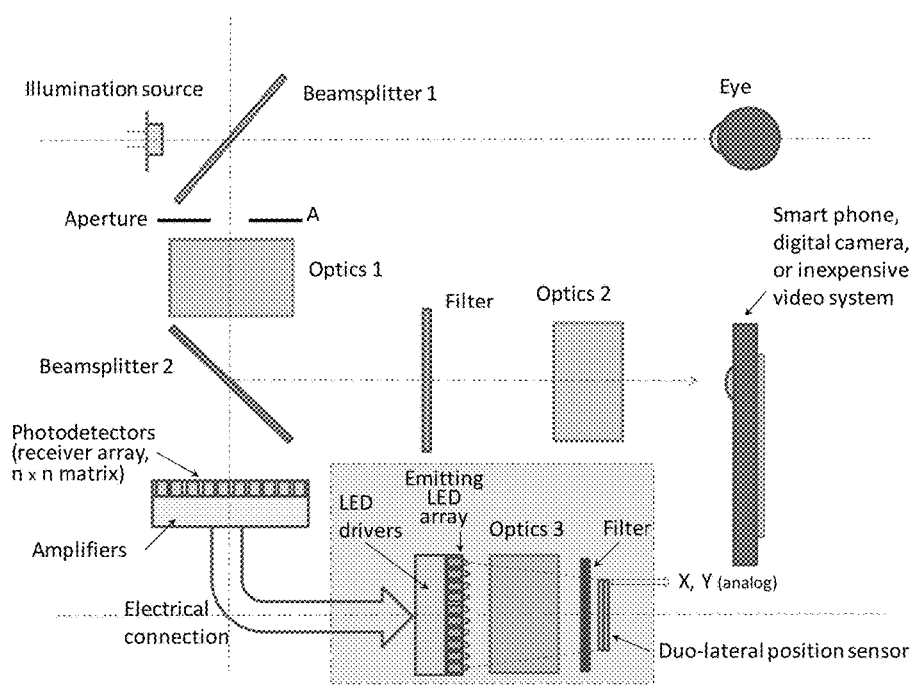
FIG. 6 illustrates a schematic diagram of image intensification using a receiving photodiode array and an emitting LED array before the duo-lateral PSD.

FIG. 6 illustrates a schematic diagram of image intensification using a photodiode array and a LED array before the duo-lateral PSD. With the device and method illustrated in FIG. 6, light from an illumination light source (i.e. NIR LED or NIR laser diode) illuminates the pupil. Because the NIR light reflected from the retina is focused back by the eye's optics toward the source, the pupil appears significantly brighter than the eyelids, sclera, or iris in the NIR spectral region. This is especially the case when the light retroreflected from the retina passes through an aperture conjugate to the light source. This aperture stop blocks most of the light diffusely reflected from the lids, sclera, and iris. Beamsplitter 1, as illustrated in FIG. 6 deflects returning light toward the measurement/monitoring path, while after optical scaling and focusing (Optics 1), Beamsplitter 2 splits the received light between the monitoring system (ca. 10%) and measurement system (ca. 90%). The image going to the monitoring system is separately focused by Optics 2.

The measurement system receives the light as an image of the pupil by means of a matrix of photodetectors (photodiodes, PIN photodiodes, or avalanche photodiodes). After amplification, the analog signal from each individual photodetector is communicated electrically to an array of LEDs, each with its own driver. Each LED is thus controlled in a proportional manner by the signal (amount of light) received by a corresponding receiver (photodetector). The light from the LED array is then focused appropriately by a third optical assembly, Optics 3, onto a duo-lateral PSD, which delivers directly the X- and Y-coordinate as analog signals with a bandwidth that can easily exceed 5 kHz, and can be directly digitized, thus registering the position of the pupil without any image processing, at a speed which cannot be achieved by present video-based systems.

The device and method of FIG. 6 allow for the intensity of the LEDs to be controlled over a very wide range (also with the help of a microcontroller), thus providing the ability to work above the sensitivity threshold of the PSD. This increases drastically the signal-to-noise (S/N) ratio and ensures reliable performance. The emission spectrum of the LEDs can be chosen such that they match closely the spectral sensitivity of the PSD. The operation of the photodetector-LED emitter block is very fast, because there is no scanning or modulation and no real-time signal processing involved. Thus, the speed of the image intensification matches the speed of the PSD. The connection between the photodetectors/amplifiers and LED drivers is electrical, which makes it easier to develop a folded, more compact optomechanical design. The inclusion of the monitoring camera guarantees that the pupil is within the field of view of the device for better aiming, and helps monitor the quality of the signal. Best quality will be achieved when using an inexpensive CCTV video camera sensitized in the NIR region. Higher spatial density can be achieved by fabricating denser receiver and emitter arrays.

Figure 7:
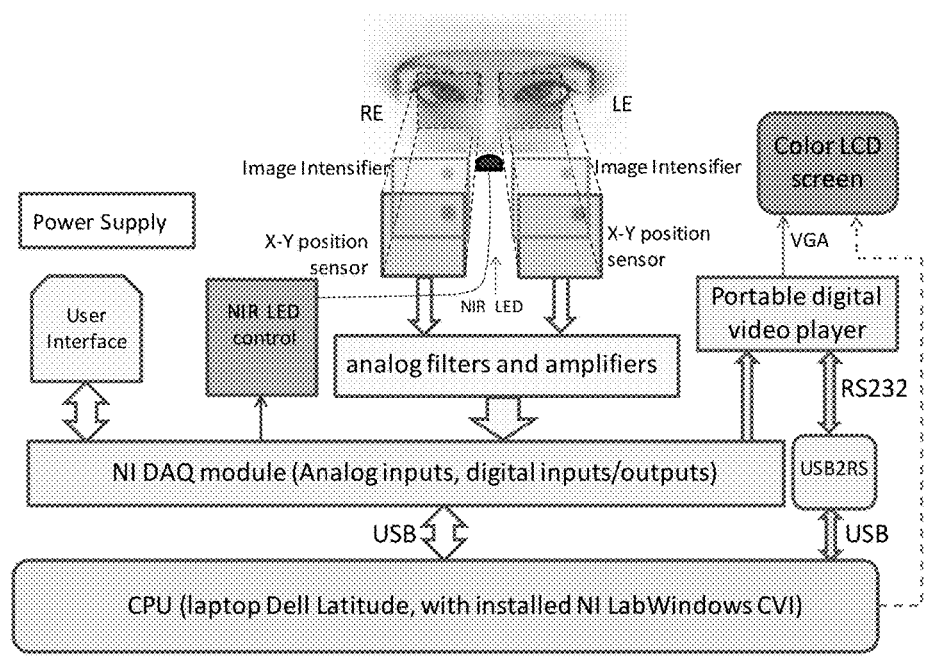
FIG. 7 illustrates a block diagram of eye tracking using image intensifiers and analog position sensing detectors.

In the non-optically-aligned design illustrated schematically in FIG. 7, analog position sensing detectors (PSD) are used, (also shown in FIG. 3). FIG. 7 illustrates a flow diagram of eye tracking using image intensifiers and analog position sensing trackers. The 40×40 mm "entrance pupils" for the left eye (LE) and right eye (RE) are imaged onto two 10×10 mm dual-axis (duolateral), highly linear, position-sensing photodiodes (for example position-sensing photodiodes from First Sensor Inc, DL100-7PCBA3, 250 kHz; ca. $200 ea). The light coming from each eye is first intensified by an image intensifier. As light impinges on each PSD, bipolar analog signals are produced, representing the X and Y positions of the centroid of the light power density. The analog signals are then fed to an analog module for analog filtering and final amplification, and from there to a data acquisition module. The eye-tracking process is thus reduced to digitizing two analog signals, plus the two sums of the currents for X and Y, for normalization purposes, if needed. This can easily be done at speeds of hundreds of samples/sec/channel, and enables very fast performance, suitable for acquiring and processing very fast signals at speeds out of reach for standard video systems.

Figure 8:
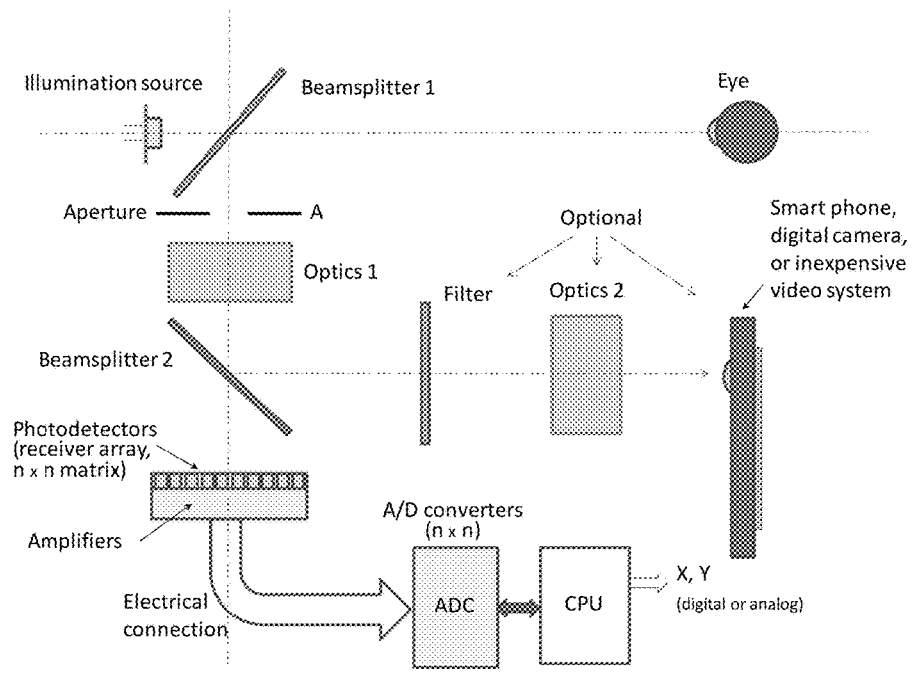
FIG. 8. illustrates a schematic diagram of another embodiment of a device and method according to the present invention. All signals from a receiving photodetector array are amplified and digitized.
Figure 9:
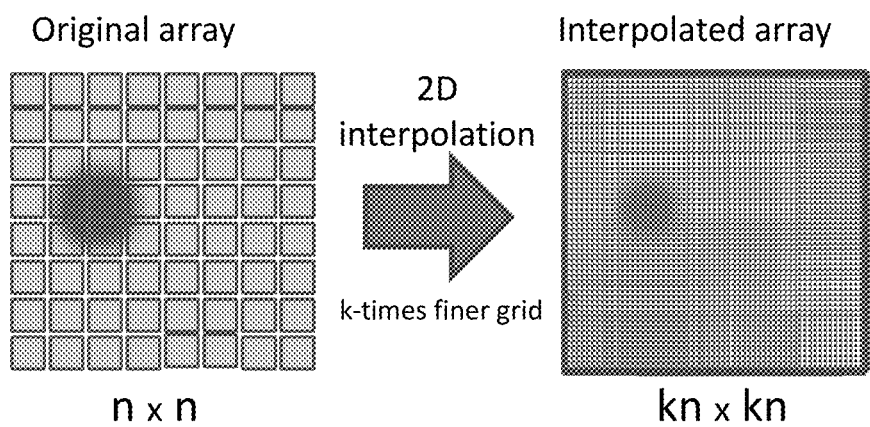
FIG. 9 illustrates a schematic view of finding the precise location of the pupil on a finer grid using interpolation.

FIG. 8 illustrates a schematic diagram of another embodiment of a device and method according to the present invention. With this method, the n×n signals coming from the amplifiers of each of the photodetectors in a photodetector array (PIN or Avalanche photodiode arrays, CCD, or CMOS arrays, etc.) are connected to the n×n inputs of an analog-to-digital converter module, as illustrated in FIG. 8. After digitization, the n×n image is resampled onto a k-times finer grid (FIG. 9, n=8) by means of 2D interpolation (nearest-neighbor interpolation, bilinear interpolation, bicubic interpolation, inverse distance weighting, kriging (Gaussian process regression), or other. The spot of maximum intensity is then found by a fast algorithm (using for example Newton's steepest descent method, or other, starting from the previous pupil position). The coordinates of this maximum are assumed to be the X- and Y-coordinates of the current pupil position. FIG. 9 illustrates a schematic view of finding the precise location of the pupil on a finer grid. The precision of this method is influenced by the original size (n×n) of the photodetector array, by the fine-grid factor k, as well as by the type of interpolation algorithm used. The same factors influence the speed of the algorithm. If higher sampling rates are desirable, data acquisition can be performed at high speed (much higher than with video systems), while analysis would be performed off-line. The device and method associated with FIG. 9 can provide a higher sensitivity to low light, with no need for an analog PSD, and the precision can be controlled though software (by defining the secondary grid size). The embodiment based on FIG. 8 and FIG. 9 includes photodetector arrays for precise pupil detection by means of increasing the spatial resolution using 2D interpolation methods. This embodiment can allow for precise detection of pupil position with sensor arrays with a lower than otherwise number of individual sensor cells.

Figure 10:
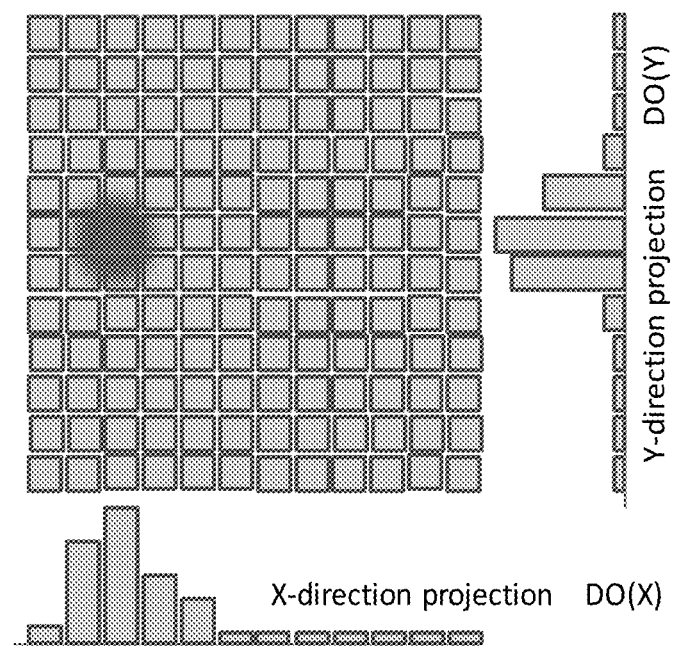
FIG. 10 illustrates a conceptual view of a profile sensor for light spot detection.

With video-based eye trackers, the main limiting factor today is the readout logic. While 2D photodiode arrays (such as PIN and avalanche type) lack the necessary spatial resolution, existing CCD, CMOS, and RACID (Random access Charge Injection Devices, typically silicon CMOS) arrays can be made sensitive enough at high spatial and bit resolution, but at the price of slow readout which slows down the overall performance. High definition image acquisition and processing hardware solutions have been offered (i.e. AD9978 and ADDI7004) containing fast analog-to-digital converters (ADC) for X and Y, but still not sufficiently fast to deliver a high enough frame rate needed for high-speed eye tracking. A possible solution is to use, as illustrated in FIG. 10, a so-called profile sensor, to track just the position of the pupil. Profile sensors are image sensors that provide not all pixels, but rather the sums over columns and rows, thus building the X- and Y-projection profiles. The projection profiles in the X and Y directions have very small amounts of data (2n) compared with "standard" area sensors ($n^2$) and therefore allow high-speed position detection of moving objects, also allowing for detection of multiple spots of light.

Figure 11:
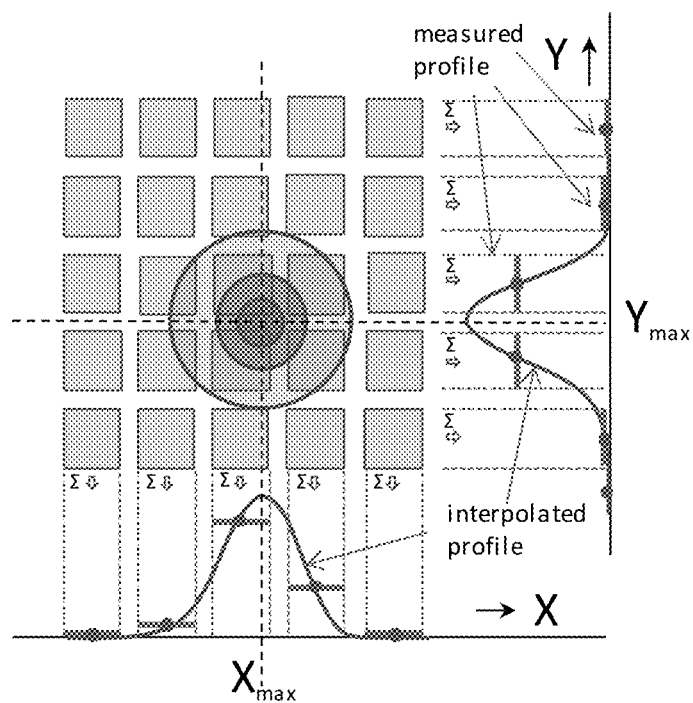
FIG. 11 illustrates a simplified diagram of the interpolation process on a 5×5 array using 1D interpolation for each axis.

To improve spatial precision, especially with small numbers n, one-dimensional interpolation may be used for each profile. FIG. 11 illustrates a simplified diagram of the interpolation process on a 5×5 array. The location of the pupil image for each frame can be calculated after interpolating the X- and the Y-profiles, and finding the coordinates of the profile maxima X. and Ymax. Should multiple local maxima occur, then a least squares cubic or quadratic polynomial interpolation is employed, to calculate the polynomial coefficients in terms of minimum sum of the squares of the residuals. Using interpolation increases the resolution by a factor of 10, thus matching the resolution of the highest resolution imaging arrays for the purpose of detecting the pupil position. With an exit pupil of 30×30 mm, after interpolation on a 7× finer grid, a "pixel" resolution of 17 µm, or 0.1° of visual angle is achieved.

With respect to the profile sensor (FIG. 10, FIG. 11), both projection profiles can be obtained by either analog or digital summation.

Figure 12:
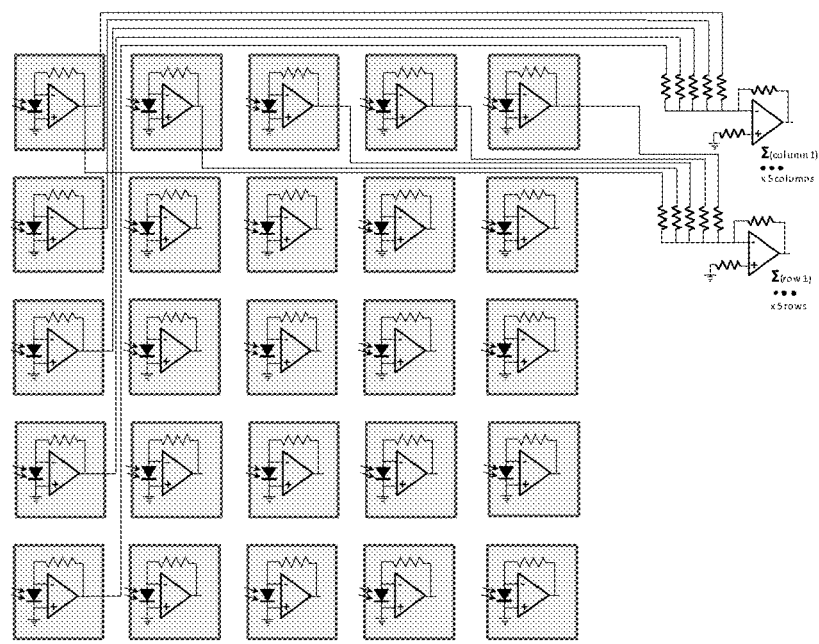
FIG. 12 illustrates a schematic view of an example of an analog profile sensor, showing the sums for only column 1 and row 1 of a 5×5 array (n=5).

The analog version of the profile sensor is explained using FIG. 12. For simplicity, FIG. 12 illustrates a schematic view of an example showing the sums for only column 1 and row 1 of a 5×5 array (n=5). All n columns and all n rows of the array are separately summated in hardware by means of additional n+n=2n summing amplifiers, to produce two orthogonal projection profiles. This summation can be made very fast, so that the sums for all rows and columns appear at the 2n analog outputs almost simultaneously. For improved clarity, the transimpedance amplifiers for every detector are shown as well, although they are usually not part of the photodetector array. The n=5 column sums provide the projection of the image onto the X-axis (X-profile), while the n=5 row sums provide the projection of the same image onto the Y-axis (Y-profile). The profiles obtained are of the type shown in FIG. 10. After digitization of the column and row sum signals, 1D interpolation on a finer grid can be performed (especially when n is a small number), using standard methods (spline, nearest neighbor, or other). Finally, the maxima are found separately for the X- and Y-interpolated profile, and their locations are declared as the X- and Y-locations of the pupil. Thus, data need to be acquired from 2n signals, instead of the n×n signals with the previous method. With only 2n additional summing amplifiers, acquisition and signal processing times are strongly reduced. The device and method associated with FIGS. 10-12 are much faster, and the number of signals to be sampled (ADC channels) is (n/2) times smaller.

With respect to FIG. 10, instead of the analog projection profile sensor described under the methods described further herein, a digital profile sensor can be employed in order to obtain the X- and Y-projection profile of the image of the pupil. Columns and rows are summed by switching the participating CMOS detector elements to an integrating summing charge amplifier. Once all elements of a column (or respectively a row) have been summed (by means of analog integration), the sum is converted to a digital value by an ADC (typically one for X- and one for Y-), and transmitted to the CPU in a serial manner. A full profile acquisition is completed after all columns and respectively all rows are read and transmitted to the CPU.

The projection profiles in the X and Y directions have very small amounts of data (2n measurements per frame) compared with "standard" area sensors ($n^2$ measurements per frame) and therefore allow high-speed position detection of moving objects, also allowing for detection of multiple spots of light. There are commercially available CMOS digital profile sensors, of resolution 256×256, i.e. 256 in X- and Y-direction, respectively, with serial interface. Should a higher resolution be necessary, 1D interpolation can be used, separately for the X- and the Y-profile. The method associated with FIG. 10 gives relatively higher pixel resolution, compared with the photodiode arrays. A much smaller amount of data is used, compared with full-size photodetector arrays. It has potentially higher speed, if no interpolation is used, improved linearity compared with purely analog PSD, and digital output.

Figure 13:
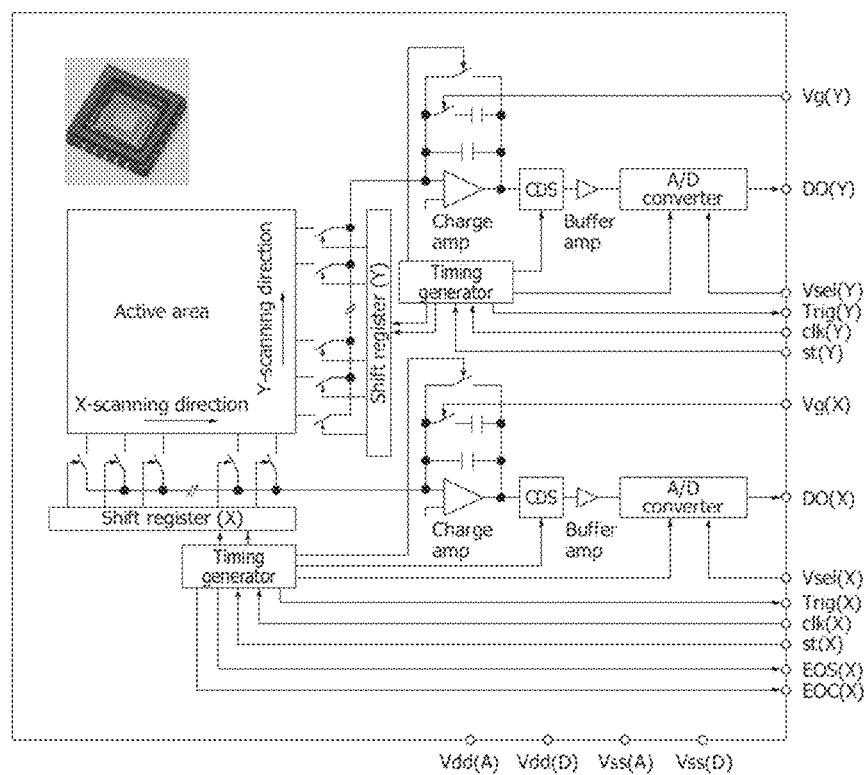
FIG. 13 illustrates a circuit diagram view of the internal diagram of Hamamatsu's S9132 profile sensor (a 256×256 array) providing a frame rate of 3200 frames/s (8 bit) or 1600 frames/s (10 bit).
Figure 14:
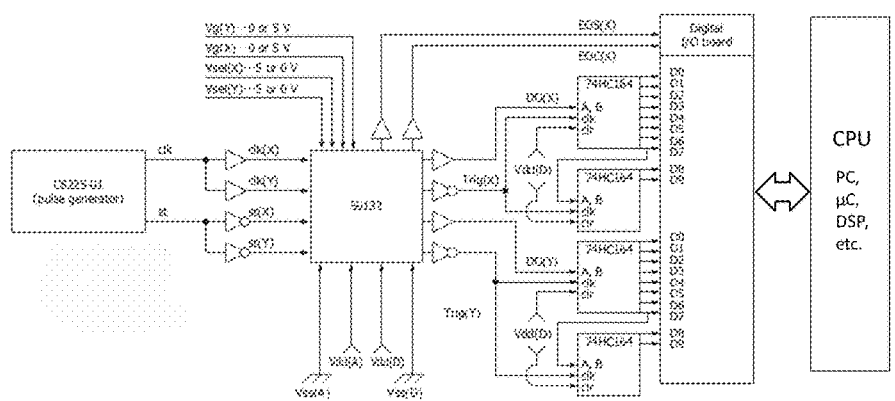
FIG. 14 illustrates a circuit board view of interfacing the profile sensor S9132 to the CPU.

FIG. 13 illustrates a circuit diagram view of the internal diagram of Hamamatsu's S9132 profile sensor (a 256×256 array providing a frame rate of 3200 frames/s (8 bit) or 1600 frames/s (10 bit). Two timing generators, a bias voltage generator, two integrating charge amplifiers, readout circuitry (shift registers), and two 10-bit ADCs circuits are all integrated on the same chip, allowing operations with a relatively simple external driver circuit and an external signal processing circuit. ADC resolution and analog gain can be controlled over Vsel(X)/Vsel(Y), and Vg(x)/Vg(Y), respectively. Profile data for X and Y (256 sums for each) are provided serially on outputs DO(X) and DO(Y). Signal EOC (End-of-Conversion) informs the external logic that one sum has been transmitted serially outwards, while EOS (End-of-Scan) signals the end of a frame. Interfacing to a PC or to any other CPU (central processing unit, such as a microcontroller or a digital signal processor) is shown in FIG. 14. FIG. 14 illustrates a circuit board view of interfacing the profile sensor S9132 to the CPU. Here, the serial data are de-serialized and provided to the CPU in a parallel form. A serial interface would also be possible and can be implemented on a microcontroller-based version of the device. To provide external timing, Hamamatsu's pulse generator C8225-01 will be used at 5 MHz for the 10-bit mode, or 10 MHz for the 8-bit mode.

The present invention can also use the USB-6509 DIO (digital input/output) board from National Instruments, which has 96 TTL/CMOS compatible digital channels, and high current drive of 24 mA sink or source). For each eye, should 10-bit ADC mode be implemented, four 8-bit ports for data will be used, i.e. eight 8-bit ports (64 DIO lines) will be needed for both eyes. The remaining 32 lines will be used for control signals to/from the profile sensors, and for user interface.

The software may be written in any programming language that can be optimized for fast execution speed. An appropriate choice would be, for example, LabWindows CVI (C-language with enhanced peripheral driver capabilities and GUI features) from National Instruments. However any suitable software and programming language for implementing the invention can also be used. After acquiring the X- and Y-profiles for each frame, the coordinates (in a range 0 . . . 255) of the maxima for X and Y are found. If needed, local interpolation is performed, to find the precise location of the bright spot produced by the pupil. Analysis can be sped by analyzing only a region of interest (ROI) around the previously detected pupil location.

For less demanding applications the device works with the non-interpolated pixel resolution of 256×256. This works in real time at the full data acquisition speed of the sensor. For applications demanding higher precision, Lagrange polynomial interpolation is used, to pass a cubic polynomial through the measured 10-15 values in the vicinity of the maximum. The cubic type will cover possible asymmetries while keeping the computation time low.

Figure 15:
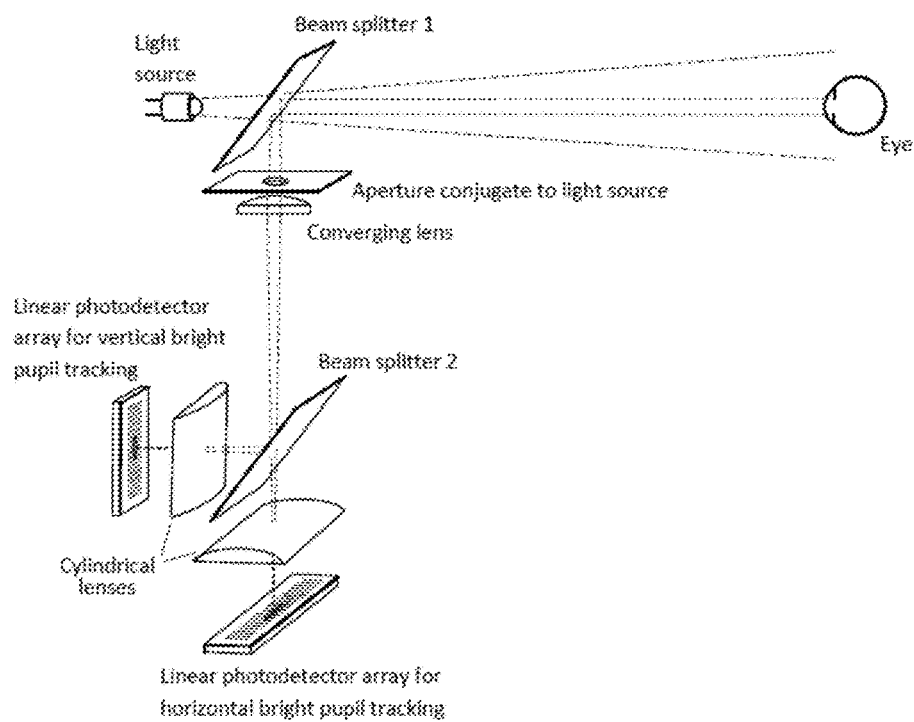
FIG. 15 illustrates a schematic diagram of a bright pupil eye tracker using separate X and Y linear photodetector arrays.

An additional embodiment of the present invention is illustrated in FIG. 15. With the eye looking at the light source, light retro-reflected from the retina is imaged back by the eye toward the light source, and a portion of this light is deflected via beam splitter 1 to pass through the aperture conjugate to the light source. This conjugate aperture enhances the intensity of the bright pupil while minimizing returning light from external reflections. The converging lens images the bright pupil onto the surfaces of the linear photodetector arrays via beam splitter 2. The cylindrical lenses narrow the images of the bright pupil onto the linear photodetector arrays into narrow ovals such that any light from the converging lens that passes through the square apertures of the cylindrical lenses strikes the linear photodetector arrays within their active areas. The square apertures of the cylindrical lenses are imaged in the reverse direction by the converging lens to a position near the eye, defining an aerial square entrance pupil for the device.

The positions of the images of the bright pupil along the vertical and horizontal linear photodetector arrays are determined rapidly and simultaneously by conventional electronic means known to the art, thus tracking the bright pupil by providing pairs of X and Y coordinates in rapid succession.

Computer control, calculations, and display may be executed on a personal computer (PC) with a non-transitory computer readable medium. Alternately, an imbedded control/computing system for portability and miniaturization can be implemented. This will create a better environment for experimentation, and will minimize the risk of failure.

Finally, if the position detectors can truly replace video systems, then the addition of simultaneously tracked infrared spots of light, as described above, using additional position detectors, can provide conventional calibrated eye tracking and thus can revolutionize this entire field, providing simpler and less costly apparatus to enable eye control of external devices such as smart phones, tablet computers, aiming devices, manufacturing machinery, and aids for the disabled. Because position detectors should be able to provide eye tracking at much faster sampling rates than video systems, the entire field of medical eye movement research may benefit from simpler, less costly, and higher fidelity recording devices. This is therefore a potentially broad transformative prospect.

It should be noted that the device and method of the present invention can be executed using a computing device such as a microprocessor, hard drive, solid state drive, or any other suitable computing device known to or conceivable by one of skill in the art. The computing device may be programmed with a non-transitory computer readable medium that is programmed with steps to execute the different stimulation levels, patterns, and configurations available.

Any such computer application will be fixed on a non-transitory computer readable medium. It should be noted that the computer application is programmed onto a non-transitory computer readable medium that can be read and executed by any of the computing devices mentioned in this application. The non-transitory computer readable medium can take any suitable form known to one of skill in the art. The non-transitory computer readable medium is understood to be any article of manufacture readable by a computer. Such non-transitory computer readable media include, but are not limited to, magnetic media, such as floppy disk, flexible disk, hard, disk, reel-to-reel tape, cartridge tape, cassette tapes or cards, optical media such as CD-ROM, DVD, blu-ray, writable compact discs, magneto-optical media in disc, tape, or card form, and paper media such as punch cards or paper tape. Alternately, the program for executing the method and algorithms of the present invention can reside on a remote server or other networked device. Any databases associated with the present invention can be housed on a central computing device, server(s), in cloud storage, or any other suitable means known to or conceivable by one of skill in the art. All of the information associated with the application is transmitted either wired or wirelessly over a network, via the interne, cellular telephone network, or any other suitable data transmission means known to or conceivable by one of skill in the art.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A fast device for detecting rapid movements of an eye of a subject by tracking an image of the pupil of the eye, comprising:
   a light source configured for delivering light to an eye of the subject, wherein the light entering the pupil of the eye is retro-reflected by the fundus of the eye back toward the light source;
   optical means for capturing the light retro-reflected by the fundus of the eye to form a bright image of the pupil of the eye;
   a position-sensing detector configured to receive the bright image of the pupil of the eye, wherein the position-sensing detector senses X- and Y-positions of the bright image of the pupil of the eye; and wherein the position-sensing detector is further configured to extract only a minimum amount of information necessary to determine X- and Y-coordinates of an intensity centroid of said bright image on the detector along only two orthogonal axes provided by the X- and Y-coordinates;
   a means for low-throughput transmission and storage of said minimum amount of information to a digital processing unit;
   and
   a means for digital analysis of said minimum position-sensing information to generate an output characterizing movements of the eye.

2. The device of claim 1 wherein the position-sensing detector comprises a duo-lateral position sensor, further wherein the duo-lateral position sensor delivers X- and Y-coordinates in immediately available analog form for each of the X- and Y-coordinates.

3. The device of claim 2 further comprising an image intensifier that receives the image of the bright pupil from said optical means and delivers an intensified version of the image of the bright pupil to said duo-lateral position sensor.

4. The device of claim 3 wherein said image intensifier includes a coherent microchannel plate serving as an electron multiplier and accelerator for each microchannel in the plate, producing a pixelated rendition of the intensified pupil image for conveyance to the position-sensing detector.

5. The device of claim 3 wherein said image intensifier comprises a photodiode array and a conjugate array of light emitting diodes (LEDs), wherein the output of each photodetector is amplified and used to drive the corresponding LED in the conjugate array of LEDs, creating a pixelated rendition of the intensified pupil image for conveyance to the position-sensing detector.

6. The device of claim 1 wherein said position-sensing detector comprises an array of n×m photodiodes wherein the output signals are not read out individually, but are rather summed row-wise and column-wise by analog adders to build the X- and Y-profiles of the image of the bright pupil, as projections onto the X- and Y-axes, and are digitized as n+m intensity values, allowing the intensity centroid of the bright pupil image to be determined from the maxima of the X- and Y-profiles in 1D context (one dimension) for the corresponding directions of eye movement to be detected.

7. The device of claim 6 wherein the maxima of the X- and Y-profiles are determined by 1D interpolation.

8. The device of claim 1 wherein said position-sensing detector comprises an array of n×m avalanche photodetectors wherein the output signals are not read out individually, but are rather summed row-wise and column-wise to build the X- and Y-profiles of the image of the bright pupil, as projections onto the X- and Y-axes, and are digitized as n+m intensity values, allowing the intensity centroid of the pupil image to be determined from the maxima of the X- and Y-profiles in 1D context (one dimension) for the corresponding directions of eye movement to be detected.

9. The device of claim 8 wherein the maxima of the X- and Y-profiles are determined by 1D interpolation.

10. The device of claim 1 wherein said position-sensing detector comprises a digital n×m profile sensor of n rows and m columns of pixels wherein the output signals are the digitized sums of the n rows and m columns, to build the X- and Y-profiles of the image of the bright pupil, as projections onto the X- and Y-axes, allowing the intensity centroid of the pupil image to be determined from the maxima of the X- and Y-profiles in 1D context (one dimension) for the corresponding directions of eye movement to be detected.

11. The device of claim 10 wherein the maxima of the X- and Y-profiles are determined by 1D interpolation.

12. The device of claim 10 further comprising an image intensifier in the form of a microchannel plate that receives the image of the bright pupil from said optical means and delivers an intensified version of the image of the bright pupil to said profile sensor.

13. The device of claim 1 wherein said position-sensing detector comprises two separate linear photodetector arrays aligned respectively along the two orthogonal axes, X- and Y-, whereby each linear photodetector array receives an image of the bright pupil for detection of an intensity profile along the array for use in identifying the position of the intensity centroid of said image on the linear photodetector array, supplying one of the X- and Y-coordinates, with the other linear photodetector array supplying the other of the X- and Y-coordinates.

14. A method for detecting rapid movements of an eye of a subject by tracking an image of the pupil of the eye, comprising:
   delivering light to an eye of the subject, wherein the light entering the pupil of the eye is retro-reflected by the fundus of the eye back toward the light source;
   capturing the light retro-reflected by the fundus of the eye to form a bright image of the pupil of the eye;
   receiving the bright image of the pupil of the eye;
   sensing X- and Y-positions of the bright image of the pupil of the eye;
   extracting only a minimum amount of information necessary to determine X- and Y-coordinates of the intensity centroid of said bright image on a detector along only two orthogonal axes provided by the X- and Y-coordinates;
   low-throughput transmitting and storing of said minimum amount of information to a digital processing unit; and
   receiving information from the position-sensing detector to generate an output characterizing movements of the eye.

15. The method of claim 14 further comprising receiving the image of the bright pupil from said optical means and delivering the image of the bright pupil to a duo-lateral position sensor.

16. The method of claim 14 further comprising receiving the image of the bright pupil with an image intensifier from said optical means and delivering an intensified version of the image of the bright pupil to said duo-lateral position sensor.

17. The method of claim 14 further comprising determining maxima on X- and Y-profiles using one-dimensional (1D) interpolation.

18. The method of claim 14 further comprising using an image intensifier with a photodiode array and a conjugate array of light emitting diodes (LEDs), wherein the output of each photodetector is amplified and used to drive the corresponding LED in the conjugate array of LEDs, creating a pixelated rendition of the intensified pupil image for conveyance to the position-sensing detector.

19. The method of claim 14 further comprising using an image intensifier in the form of a microchannel plate that receives the image of the bright pupil from said optical means and delivers an intensified version of the image of the bright pupil to a profile sensor.

20. The method of claim 14 further comprising using a position-sensing detector which comprises two separate linear photodetector arrays aligned respectively along the two orthogonal axes whereby each linear photodetector array receives an image of the bright pupil for detection of an intensity profile along each of the X- and Y-axes for use in identifying the position of the intensity centroid of said image on the linear photodetector.

21. A fast device for detecting rapid movements of an eye of a subject by tracking an image of the pupil of the eye, comprising:
a light source configured for delivering light to an eye of the subject, wherein the light entering the pupil of the eye is retro-reflected by the fundus of the eye back toward the light source;
optical means for capturing the light retro-reflected by the fundus of the eye to form a bright image of the pupil of the eye;
a position-sensing detector configured to receive the bright image of the pupil of the eye and to extract only a minimum amount of information necessary to determine the position of the intensity centroid of said bright image on the detector along only two orthogonal axes;
a means for low-throughput transmission and storage of said minimum amount of information to a digital processing unit;
a means for digital analysis of said minimum position-sensing information to generate an output characterizing movements of the eye; and
wherein said position-sensing detector comprises an array of n×m pixel sensors wherein the output signals are not read out individually, but are rather summed row-wise and column-wise by analog adders to build X- and Y-profiles of the image of the bright pupil, as projections onto X- and Y-axes, and are digitized as n+m intensity values, allowing the intensity centroid of the bright pupil image to be determined from the maxima of the X- and Y-profiles in 1D context (one dimension) for the corresponding directions of eye movement to be detected.

22. A fast device for detecting rapid movements of an eye of a subject by tracking an image of the pupil of the eye, comprising:
a light source configured for delivering light to an eye of the subject, wherein the light entering the pupil of the eye is retro-reflected by the fundus of the eye back toward the light source;
optical means for capturing the light retro-reflected by the fundus of the eye to form a bright image of the pupil of the eye;
a duo-lateral position sensor, further wherein the duo-lateral position sensor delivers X- and Y-coordinates in immediately available analog form for each of the X- and Y-coordinates, wherein the duo-lateral position sensor is configured to receive the bright image of the pupil of the eye and to extract only a minimum amount of information necessary to determine the position of the intensity centroid of said bright image on the detector along only two orthogonal axes;
a means for low-throughput transmission and storage of said minimum amount of information to a digital processing unit; and,
a means for digital analysis of said minimum position-sensing information to generate an output characterizing movements of the eye.

* * * * *